US 11,767,386 B2

United States Patent
Hoshika et al.

(10) Patent No.: US 11,767,386 B2
(45) Date of Patent: Sep. 26, 2023

(54) HOT-WATER-STERILIZED PACKAGING AND METHOD FOR PRODUCING SAME

(71) Applicant: KURARAY CO., LTD., Kurashiki (JP)

(72) Inventors: Rina Hoshika, Kurashiki (JP); Makoto Okamoto, Kurashiki (JP); Makoto Suzuki, Kurashiki (JP)

(73) Assignee: KURARAY CO., LTD., Kurashiki (JP)

( * ) Notice: Subject to any disclaimer, the term of this patent is extended or adjusted under 35 U.S.C. 154(b) by 673 days.

(21) Appl. No.: 16/474,822

(22) PCT Filed: Dec. 28, 2017

(86) PCT No.: PCT/JP2017/047335
§ 371 (c)(1),
(2) Date: Jun. 28, 2019

(87) PCT Pub. No.: WO2018/124296
PCT Pub. Date: Jul. 5, 2018

(65) Prior Publication Data
US 2019/0345280 A1    Nov. 14, 2019

(30) Foreign Application Priority Data

Dec. 29, 2016 (JP) .................................. 2016-257385

(51) Int. Cl.
*A61L 2/04* (2006.01)
*B32B 27/08* (2006.01)
(Continued)

(52) U.S. Cl.
CPC .............. *C08F 216/38* (2013.01); *A61L 2/04* (2013.01); *B32B 27/08* (2013.01); *B32B 27/306* (2013.01);
(Continued)

(58) Field of Classification Search
CPC ....... A61L 2/04; A61L 2203/23; B32B 27/30; B32B 27/306; B32B 2439/00;
(Continued)

(56) References Cited

U.S. PATENT DOCUMENTS 4,929,482 A * 5/1990 Moritani ............ B65D 81/3415
428/688
4,960,639 A * 10/1990 Oda ...................... B32B 27/306
428/323

(Continued)

FOREIGN PATENT DOCUMENTS

JP    2009-242591 A    10/2009
JP    2010-59418 A     3/2010
(Continued)

OTHER PUBLICATIONS

International Search Report dated Mar. 27, 2018 in PCT/JP2017/047335 filed on Dec. 28, 2017.
U.S. Appl. No. 16/474,771, filed Jun. 28, 2019, Makoto Okamoto.

*Primary Examiner* — Michael C Romanowski
(74) *Attorney, Agent, or Firm* — Oblon, McClelland, Maier & Neustadt, L.L.P.

(57) ABSTRACT

A hot-water sterilized package includes a container having a barrier layer filled with contents, wherein the barrier layer contains 96 mass % or more of a modified ethylene-vinyl alcohol copolymer based on the resin total, the modified ethylene-vinyl alcohol copolymer is represented by a following formula (I), contents (mol %) of a, b, and c based on the total monomer units satisfy following formulae (1) through (3), a degree of saponification (DS) defined by a following formula (4) is 90 mol % or more, and in measurement using a differential scanning calorimeter (DSC), crystalline melting enthalpy ($\Delta H_A$: J/g) during temperature rise in a hydrated state and crystalline melting enthalpy (Continued)

($\Delta H_B$: J/g) during temperature rise after drying and melting followed by rapid cooling satisfy following formulae (5) and (6). A container constituting such a package has excellent in oxygen barrier properties even after hot-water sterilization, and thus degradation of content quality is inhibited for a long period.

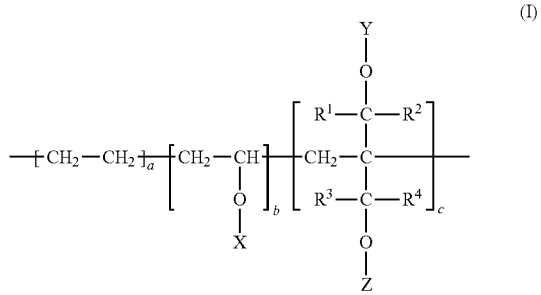

(I)

$18 \leq a \leq 55$      (1)

$0.01 \leq c \leq 20$      (2)

$[100-(a+c)] \times 0.9 \leq b \leq [100-(a+c)]$      (3)

DS=[(Total Number of Moles of Hydrogen Atoms in $X, Y,$ and $Z$)/(Total Number of Moles of $X, Y,$ and $Z$)]×100      (4)

$\Delta H_A/\Delta H_B \geq 0.5$      (5)

$\Delta H_B \geq 70$      (6).

4 Claims, 2 Drawing Sheets

(51) Int. Cl.
| | |
|---|---|
| *B32B 27/30* | (2006.01) |
| *B65B 55/02* | (2006.01) |
| *B65D 65/40* | (2006.01) |
| *C08F 216/38* | (2006.01) |
| *B32B 27/32* | (2006.01) |

(52) U.S. Cl.
CPC ............. *B32B 27/32* (2013.01); *B65B 55/02* (2013.01); *B65D 65/40* (2013.01); *A61L 2202/23* (2013.01); *B32B 2250/03* (2013.01); *B32B 2250/246* (2013.01); *B32B 2250/40* (2013.01); *B32B 2307/7244* (2013.01); *B32B 2439/00* (2013.01); *C08F 2800/10* (2013.01)

(58) Field of Classification Search
CPC ........ B32B 2250/03; B32B 2307/7244; B65B 55/02; C08L 23/0846; C08L 23/0853; C08L 23/086
See application file for complete search history.

(56) References Cited

U.S. PATENT DOCUMENTS

| | | | |
|---|---|---|---|
| 2009/0274843 A1* | 11/2009 | Oosaki | C08J 5/18 524/556 |
| 2011/0135950 A1 | 6/2011 | Okamoto et al. | |
| 2011/0178222 A1* | 7/2011 | Kani | C08J 3/226 524/503 |
| 2012/0279176 A1* | 11/2012 | Kitahara | B32B 25/08 53/425 |
| 2015/0210788 A1 | 7/2015 | Okamoto et al. | |
| 2017/0183493 A1 | 6/2017 | Okamoto | |
| 2017/0267851 A1 | 9/2017 | Yamakoshi et al. | |

FOREIGN PATENT DOCUMENTS

| | | | | |
|---|---|---|---|---|
| JP | 2014-034647 | * | 2/2014 | ............ B32B 27/28 |
| JP | 2014-34647 A | | 2/2014 | |
| JP | 2015-151428 | * | 8/2015 | ............ B29C 47/00 |
| JP | 2015-151428 A | | 8/2015 | |
| WO | WO 2015/115511 A1 | | 8/2015 | |
| WO | WO 2015/174396 A1 | | 11/2015 | |

* cited by examiner

HOT-WATER-STERILIZED PACKAGING AND METHOD FOR PRODUCING SAME

TECHNICAL FIELD

The present invention relates to a hot-water sterilized package comprising a modified ethylene-vinyl alcohol copolymer and a method of producing the same.

BACKGROUND ART

Ethylene-vinyl alcohol copolymers (hereinafter, may be abbreviated as EVOH) are resins exhibiting excellent gas barrier properties to odor, flavor, and the like and are preferably used for packaging containers for foods and the like. Such a packaging container is then filled with contents such as foods to form a package, which may be heat treated with hot water or water vapor for sterilization (hereinafter, may be abbreviated as hot-water sterilization). Heat treatment of EVOH for a long time however causes problems of resin whitening and deterioration in shape retention performance for the vacuum packed contents.

Some techniques are reported to solve such problems. Patent Documents 1 and 2 describe molded articles (films, sheets, etc.) of resin compositions containing EVOH and polyimide (hereinafter, may be abbreviated as PA). However, they have a problem of appearance damage because a large amount of moisture permeates EVOH, probably due to the hydrophilicity of EVOH, causing voids in the packaging material and whitening.

As a material to solve the above problems, Patent Document 3 describes a resin composition containing PA and EVOH having structural units derived from 1,3-diacetoxy-2-methylenepropane (hereinafter, may be abbreviated as MPDAc). However, the resin composition contains PA and thus has a problem of reduction in barrier properties characteristic of EVOH.

For such reasons, a package is expected to have excellent barrier properties and the barrier properties not to be reduced even after hot-water sterilization.

PRIOR ART DOCUMENTS

Patent Documents

Patent Document 1 JP 2009-242591 A
Patent Document 2 WO 2015/174396
Patent Document 3 JP 2015-151428 A

SUMMARY OF THE INVENTION

Problems to be Solved by the Invention

The present invention has been made to solve the above problems and is to provide a package including a container filled with contents, excellent in oxygen barrier properties even after hot-water sterilization without damaging the gas barrier properties originally possessed by EVOH.

Means of Solving the Problems

The above problems are solved by providing a hot-water sterilized package, comprising a container having a barrier layer filled with contents, wherein the barrier layer contains 96 mass % or more of modified EVOH based on the resin total, the modified EVOH is represented by a following formula (I), contents (mol %) of a, b, and c based on the total monomer units satisfy following formulae (1) through (3), a degree of saponification (DS) defined by a following formula (4) is 90 mol % or more, and in measurement using a differential scanning calorimeter (DSC), crystalline melting enthalpy ($\Delta H_A$: J/g) during temperature rise in a hydrated state and crystalline melting enthalpy ($\Delta H_B$: J/g) during temperature rise after drying and melting followed by rapid cooling satisfy following formulae (5) and (6), (I)

[In the formula (I), each of $R^1$, $R^2$, $R^3$, and $R^4$ independently denotes a hydrogen atom or an alkyl group having a carbon number from 1 to 10, and the alkyl group may include a hydroxyl group, an alkoxy group, or a halogen atom. Each of X, Y, and Z independently denotes a hydrogen atom, a formyl group, or an alkanoyl group having a carbon number from 2 to 10.]

$$18 \leq a \leq 55 \quad (1)$$

$$0.01 \leq c \leq 20 \quad (2)$$

$$[100-(a+c)] \times 0.9 \leq b \leq [100-(a+c)] \quad (3)$$

$$DS = [(\text{Total Number of Moles of Hydrogen Atoms in } X, Y, \text{ and } Z)/(\text{Total Number of Moles of } X, Y, \text{ and } Z)] \times 100 \quad (4)$$

$$\Delta H_A / \Delta H_B \geq 0.5 \quad (5)$$

$$\Delta H_B \geq 70 \quad (6).$$

At this time, it is preferred that $R^1$, $R^2$, $R^3$, and $R^4$ are hydrogen atoms. It is also preferred that each of X, Y, and Z is independently a hydrogen atom or an acetyl group.

It is preferred that the container is made of a multilayer structure having layers containing any one of polyolefin, polyimide, or polyester arranged on both sides of the barrier layer.

The above problems are also solved by providing a method of producing the package, comprising: filling the container with the contents; and then sterilizing the container with hot water.

Effects of the Invention

The container constituting the package of the present invention is excellent in oxygen barrier properties even after hot-water sterilization to inhibit degradation of content quality for a long period.

MODES FOR CARRYING OUT THE INVENTION

The present invention is a hot-water sterilized package, comprising a container having a barrier layer filled with contents, wherein the barrier layer contains 96 mass % or more of modified EVOH based on the resin total, the modified EVOH is represented by a following formula (I), contents (mol %) of a, b, and c based on the total monomer units satisfy following formulae (1) through (3), a degree of saponification (DS) defined by a following formula (4) is 90 mol % or more, and in measurement using a differential scanning calorimeter (DSC), crystalline melting enthalpy ($\Delta H_A$: J/g) during temperature rise in a hydrated state and crystalline melting enthalpy ($\Delta H_B$: J/g) during temperature rise after drying and melting followed by rapid cooling satisfy following formulae (5) and (6), (I)

[In the formula (I), each of $R^1$, $R^2$, $R^3$, and $R^4$ independently denotes a hydrogen atom or an alkyl group having a carbon number from 1 to 10, and the alkyl group may include a hydroxyl group, an alkoxy group, or a halogen atom. Each of X, Y, and Z independently denotes a hydrogen atom, a formyl group, or an alkanoyl group having a carbon number from 2 to 10.]

$$18 \leq a \leq 55 \quad (1)$$

$$0.01 \leq c \leq 20 \quad (2)$$

$$[100-(a+c)] \times 0.9 \leq b \leq [100-(a+c)] \quad (3)$$

$$DS = [(\text{Total Number of Moles of Hydrogen Atoms in } X, Y, \text{ and } Z)/(\text{Total Number of Moles of } X, Y, \text{ and } Z)] \times 100 \quad (4)$$

$$\Delta H_A / \Delta H_B \geq 0.5 \quad (5)$$

$$\Delta H_B \geq 70 \quad (6).$$

[Modified EVOH]

The modified EVOH used in the present invention is represented by the above formula (I). The modified EVOH has, in addition to ethylene units and vinyl alcohol units, monomer units having a 1,3-diol structure in main chain of the copolymer and thus the crystallinity decreases compared with EVOH not containing the monomer units, so that it is possible to improve flexibility and secondary processability. Moreover, with the modified EVOH, since the 1,3-diol structure has strong hydrogen bonding strength, it is possible to reduce a decrease in barrier property caused by decrease in crystallinity.

In the above formula (I), each of $R^1$, $R^2$, $R^3$, and $R^4$ independently denotes a hydrogen atom or an alkyl group having a carbon number from 1 to 10, and the alkyl group may include a hydroxyl group, an alkoxy group, or a halogen atom. Each of X, Y, and Z independently denotes a hydrogen atom, a formyl group, or an alkanoyl group having a carbon number from 2 to 10.

In the formula (I), $R^1$, $R^2$, $R^3$, and $R^4$ may be same groups and may also be different. The structure of the alkyl group is not particularly limited and may have a branched structure and a cyclic structure in part. In addition, the alkyl group may include a hydroxyl group, an alkoxy group, or a halogen atom. $R^1$, $R^2$, $R^3$, and $R^4$ are preferably a hydrogen atom or an alkyl group having a carbon number from 1 to 5, and more preferably a hydrogen atom. A preferred example of the alkyl group may include a linear or branched alkyl group, such as a methyl group, an ethyl group, an n-propyl group, an isopropyl group, an n-butyl group, an isobutyl group, a tert-butyl group, and a pentyl group, and among all, a methyl group and an ethyl group are more preferred and a methyl group is even more preferred.

The formula (I) has a hydroxyl group in a case that X, Y, or Z is a hydrogen atom, and the formula (I) has an ester group in a case that X, Y, or Z is a formyl group or an alkanoyl group. The alkanoyl group is preferably an alkanoyl group having a carbon number from 2 to 5 and more preferably an acetyl group, a propanoyl group, a butanoyl group, and the like, and even more preferably an acetyl group. It is preferred that all of X, Y, and Z are a hydrogen atom or a mixture containing a hydrogen atom.

Monomer units containing X is usually obtained by saponifying vinyl ester. Accordingly, it is preferred that X is a mixture of a hydrogen atom with a formyl group or an alkanoyl group having a carbon number from 2 to 10. Considering availability of the monomer (vinyl acetate) and production costs, it is more preferred that X is a mixture of a hydrogen atom with an acetyl group.

Meanwhile, it is possible to produce monomer units containing Y and Z by copolymerizing unsaturated monomer units having a 1,3-diester structure, followed by saponification, and it is also possible to produce them by directly copolymerizing unsaturated monomer units having a 1,3-diol structure. Accordingly, both Y and Z may be a hydrogen atom only, or may be a mixture of a hydrogen atom with a formyl group or an alkanoyl group having a carbon number from 2 to 10, more preferably a mixture of a hydrogen atom with an acetyl group.

In the modified EVOH, contents (mol %) of a, b, and c based on the total monomer units satisfy following formulae (1) through (3).

$$18 \leq a \leq 55 \quad (1)$$

$$0.01 \leq c \leq 20 \quad (2)$$

$$[100-(a+c)] \times 0.9 \leq b \leq [100-(a+c)] \quad (3)$$

The character a denotes a content (mol %) of ethylene units based on the total monomer units, which is from 18 to 55 mol %. When the ethylene unit content is less than 18 mol %, melt formability of the modified EVOH deteriorates. The character a is preferably 22 mol % or more. In contrast, when the ethylene unit content is more than 55 mol %, barrier properties of the modified EVOH become insufficient. The character a is preferably 50 mol % or less, more preferably 40 mol % or less, and even more preferably 35 mol % or less.

The character c denotes a content (mol %) of monomer units containing Y and Z shown at the right edge of the formula (I) based on the total monomer units, which is from 0.01 to 20 mol %. When c is less than 0.01 mol %, flexibility, formability, and secondary processability of the modified EVOH become insufficient. Moreover, barrier properties after hot-water sterilization are reduced. The character c is preferably 0.05 mol % or more, more preferably 0.1 mol % or more, and even more preferably 0.2 mol % or more. In contrast, when c is more than 20 mol %, crystallinity extremely decreases and thus barrier properties, in particular barrier properties after hot-water sterilization, of the modified EVOH are reduced. The character c is preferably 10 mol % or less and more preferably 5 mol % or less. In order to have particularly excellent barrier properties, c is preferably 2.5 mol % or less and more preferably 1.5 mol % or less.

The character b denotes a content (mol %) of vinyl alcohol units and vinyl ester units based on the total monomer units. This satisfies the following formula (3).

$$[100-(a+c)] \times 0.9 \leq b \leq [100-(a+c)] \quad (3)$$

That is, in the modified EVOH, 90% or more of the monomer units other than the ethylene units and than the monomer units containing Y and Z shown at the right edge of the formula (I) is vinyl alcohol units or vinyl ester units. In a case that the formula (3) is not satisfied, the gas barrier properties become insufficient. It is preferred to satisfy the following formula (3') and more preferred to satisfy the following formula (3").

$$[100-(a+c)] \times 0.95 \leq b \leq [100-(a+c)] \quad (3')$$

$$[100-(a+c)] \times 0.98 \leq b \leq [100-(a+c)] \quad (3")$$

The modified EVOH has a degree of saponification (DS) defined by the following formula (4) of 90 mol % or more.

$$DS=[(\text{Total Number of Moles of Hydrogen Atoms in } X, Y, \text{ and } Z)/(\text{Total Number of Moles of } X, Y, \text{ and } Z)] \times 100 \quad (4)$$

In this context, the "total number of moles of hydrogen atoms in X, Y, and Z" indicates a number of moles of the hydroxyl group, and the "total number of moles of X, Y, and Z" indicates a total number of moles of the hydroxyl group and the ester group. When the degree of saponification (DS) becomes less than 90 mol %, sufficient barrier performance is not obtained and moreover thermal stability of the modified EVOH becomes insufficient and gels and aggregates are easily generated during melt molding. In addition, thermal stability decreases and thus long-run formability during high temperature molding is prone to decrease. The degree of saponification (DS) is preferably 95 mol % or more, more preferably 98 mol % or more, and even more preferably 99 mol % or more. In order to have barrier properties and thermal stability that are particularly excellent, the degree of saponification (DS) is preferably 99 mol % or more, more preferably 99.5 mol % or more, and even more preferably 99.8 mol % or more.

It is possible to obtain the degree of saponification (DS) by nuclear magnetic resonance (NMR). It is also possible to obtain the contents of the monomer units represented by a, b, and c above by NMR. In addition, the modified EVOH used in the present invention is usually a random copolymer. It is possible to confirm to be a random copolymer from NMR and results of melting point measurement.

The method of producing the modified EVOH is not particularly limited and examples of the method may include a method, comprising: obtaining a modified ethylene-vinyl ester copolymer represented by the following formula (IV) by radical polymerization of ethylene, vinyl ester represented by the following formula (II), and an unsaturated monomer represented by the following formula (III); and then saponifying it.

In the formula (II), $R^5$ denotes a hydrogen atom or an alkyl group having a carbon number from 1 to 9. The carbon number of the alkyl group is preferably from 1 to 4. Vinyl ester represented by the formula (II) is exemplified by vinyl formate, vinyl acetate, vinyl propionate, vinyl butyrate, vinyl isobutyrate, vinyl pivalate, vinyl versatate, vinyl caproate, and the like. From an economic perspective, vinyl acetate is particularly preferred.

In the formula (III), $R^1$, $R^2$, $R^3$, and $R^4$ are same as those in the formula (I). Each of $R^6$ and $R^7$ independently denotes a hydrogen atom or an alkyl group having a carbon number from 1 to 9. The carbon number of the alkyl group is preferably from 1 to 4. Examples of the unsaturated monomer represented by the formula (III) may include 2-methylene-1,3-propanediol diacetate, 2-methylene-1,3-propanediol dipropionate, 2-methylene-1,3-propanediol dibutyrate, and the like. Among all, 2-methylene-1,3-propanediol diacetate is preferably used in view of easy production. In a case of 2-methylene-1,3-propanediol diacetate, $R^1$, $R^2$, $R^3$, and $R^4$ are hydrogen atoms and $R^6$ and $R^7$ are methyl groups.

In the formula (IV), $R^1$, $R^2$, $R^3$, $R^4$, $R^5$, $R^6$, $R^7$, a, b, and c are same as those in the formulae (I) through (III). The modified ethylene-vinyl ester copolymer thus obtained is then subjected to saponification.

In addition, instead of the unsaturated monomer represented by the above formula (III), an unsaturated monomer represented by the following formula (V) may be copolymerized, and in this case, only the units derived from the unsaturated monomer represented by the above formula (II) are saponified.

(V)

In the formula (V), $R^1$, $R^2$, $R^3$, and $R^4$ are same as those in the formula (I). Examples of the unsaturated monomer represented by the formula (V) may include 2-methylene-1,3-propanediol and 2-methylene-1,3-butanediol.

The unsaturated monomers represented by the formula (III) and the formula (V) used in the present invention have high copolymerization reactivity with vinyl ester monomers, so that copolymerization reaction proceeds easily. Accordingly, it is easy to increase an amount of modification and a degree of polymerization of the modified ethylene-vinyl ester copolymer thus obtained. In addition, an amount of the unreacted unsaturated monomers remaining after polymerization is less even when the polymerization reaction is stopped at a low conversion, so that it is excellent in respect of environment and cost. The unsaturated monomers represented by the formula (III) and the formula (V) are more excellent at this point than other monomers, such as allyl glycidyl ether and 3,4-diacetoxy-1-butene, having a functional group in an allylic position and having only one carbon atom. In this context, the unsaturated monomer represented by the formula (III) has higher reactivity than the unsaturated monomer represented by the formula (V).

The mode of polymerization for production of a modified ethylene-vinyl ester copolymer by copolymerizing ethylene, vinyl ester represented by the above formula (II), and the unsaturated monomer represented by the above formula (III) or (V) may be any of batch polymerization, semi-batch polymerization, continuous polymerization, and semi-continuous polymerization.

In addition, as the method of polymerization, it is possible to employ a known method, such as a bulk polymerization method, a solution polymerization method, a suspension polymerization method, and an emulsion polymerization method. A bulk polymerization method or a solution polymerization method is usually employed, in which polymerization proceeds without solvent or in a solvent, such as alcohol. In a case of obtaining a modified ethylene-vinyl ester copolymer with a high degree of polymerization, employment of an emulsion polymerization method becomes an option.

Although a solvent used in a solution polymerization method is not particularly limited, alcohol is used preferably, and lower alcohols, such as methanol, ethanol, and propanol, for example, are more preferably used. An amount of solvent in a polymerization reaction liquid may be selected considering the intended viscosity average degree of polymerization of the modified EVOH and chain transfer of the solvent, and a mass ratio of the solvent to the total monomers contained in the reaction liquid (solvent/total monomers) is selected from a range from 0.01 to 10, preferably a range from 0.05 to 3.

A polymerization initiator used for copolymerization of ethylene, vinyl ester represented by the above formula (II), and the unsaturated monomer represented by the above formula (III) or (V) is selected in accordance with the method of polymerization from known polymerization initiators, for example, an azo initiator, a peroxide initiator, and a redox initiator. The azo initiator may include, for example, 2,2'-azobisisobutyronitrile, 2,2'-azobis(2,4-dimethylvaleronitrile), and 2,2'-azobis(4-methoxy-2,4-dimethylvaleronitrile). The peroxide initiator may include, for example, percarbonate compounds, such as diisopropyl peroxydicarbonate, di-2-ethylhexyl peroxydicarbonate, and diethoxyethyl peroxydicarbonate; perester compounds, such as t-butylperoxy neodecanoate, α-cumylperoxy neodecanoate, and acetyl peroxide; acetylcyclohexylsulfonyl peroxide; 2,4,4-trimethylpentyl-2-peroxyphenoxyacetate; and the like. Potassium persulfate, ammonium persulfate, hydrogen peroxide, and the like may be used in combination with the above initiators. The redox initiator is a polymerization initiator in which, for example, the above peroxide initiators and a reducing agent, such as sodium hydrogen sulfite, sodium hydrogen carbonate, tartaric acid, L-ascorbic acid, and rongalite, are combined. An amount of polymerization initiator is different depending on the polymerization catalyst and thus is not determined unconditionally, and it is adjusted in accordance with the polymerization rate. The amount of polymerization initiator based on vinyl ester monomers is preferably from 0.01 to 0.2 mol % and more preferably from 0.02 to 0.15 mol %. Although the polymerization temperature is not particularly limited, it is appropriately from room temperature to 150° C. approximately, and preferably not less than 40° C. and not more than a boiling point of a solvent to be used.

For copolymerization of ethylene, vinyl ester represented by the above formula (II), and the unsaturated monomer represented by the above formula (III) or (V), they may be copolymerized in the presence of a chain transfer agent as long as not inhibiting the effects of the present invention. The chain transfer agent may include, for example, aldehydes, such as acetaldehyde and propionaldehyde; ketones, such as acetone and methylethylketone; mercaptans, such as 2-hydroxyethanethiol; and phosphinates, such as sodium phosphinate monohydrate. Among all, aldehydes and ketones are used preferably. Although an amount of adding the chain transfer agent to the polymerization reaction liquid is determined in accordance with the chain transfer constant of the chain transfer agent and the intended degree of polymerization of the modified ethylene-vinyl ester copolymer, it is preferably from 0.1 to 10 parts by mass based on 100 parts by mass of the vinyl ester monomer in general.

It is possible to obtain the modified EVOH by saponifying the modified ethylene-vinyl ester copolymer thus obtained. At this time, the vinyl ester units in the copolymer are converted to vinyl alcohol units. In addition, ester bonds derived from the unsaturated monomer represented by the formula (III) are also hydrolyzed at the same time to be converted to a 1,3-diol structure. In such a manner, it is possible to hydrolyze different kinds of ester group by one saponification reaction at the same time.

It is possible to employ a known method for a method of saponifying the modified ethylene-vinyl ester copolymer. The saponification reaction is usually carried out in an alcohol or hydrous alcohol solution. Alcohol preferably used at this time is lower alcohol, such as methanol and ethanol, and more preferably methanol. Alcohol or hydrous alcohol used for the saponification reaction may contain another solvent, as long as the solvent is 40 mass % or less of its mass, such as acetone, methyl acetate, ethyl acetate, and benzene. The catalyst used for the saponification is, for example, alkali metal hydroxides, such as potassium hydroxide and sodium hydroxide; alkali catalysts, such as sodium methylate; and acid catalysts, such as mineral acid. Although the temperature to carry out the saponification is not limited, it is preferably in a range from 20° C. to 120° C. In a case that gelatinous products precipitate as the saponification proceeds, it is possible to obtain modified EVOH by grinding the products and then washing and drying them.

The modified EVOH may contain a structural unit derived from another ethylenic unsaturated monomer that is copolymerizable with ethylene, vinyl ester represented by the above formula (II), and the unsaturated monomer represented by the above formula (III) or (V) as long as not inhibiting the effects of the present invention. Such an ethylenic unsaturated monomer may include, for example, α-olefins, such as propylene, n-butene, isobutylene, and 1-hexene; acrylic acid and salts thereof; unsaturated monomers containing an acrylic ester group; methacrylic acid and salts thereof; unsaturated monomers containing a methacrylic ester group; acrylamide, N-methylacrylamide, N-ethylacrylamide, N,N-dimethylacrylamide, diacetoneacrylamide, acrylamide propane sulfonic acid and salts thereof, and acrylamidopropyl dimethylamine and salts thereof (for example, quaternary salts); methacrylamide, N-methylmethacrylamide, N-ethylmethacrylamide, methacrylamide propane sulfonic acid and salts thereof, and methacrylamidopropyl dimethylamine and salts thereof (for example, quaternary salts); vinyl ethers, such as methyl vinyl ether, ethyl vinyl ether, n-propyl vinyl ether, i-propyl vinyl ether, n-butyl vinyl ether, i-butyl vinyl ether, t-butyl vinyl ether, dodecyl vinyl ether, stearyl vinyl ether, and 2,3-diacetoxy-1-vinyloxypropane; vinyl cyanides, such as acrylonitrile and methacrylonitrile; vinyl halides, such as vinyl chloride and vinyl fluoride; vinylidene halides, such as vinylidene chloride and vinylidene fluoride; allyl compounds, such as allyl acetate, 2,3-diacetoxy-1-allyloxypropane, and allyl chloride; unsaturated dicarboxylic acids, such as maleic acid, itaconic acid, and fumaric acid, and salts thereof or esters thereof; vinylsilane compounds, such as vinyltrimethoxysilane; and isopropenyl acetates.

In the modified EVOH after hot-water sterilization of the present invention, and in measurement using a differential scanning calorimeter (DSC), crystalline melting enthalpy ($\Delta H_A$: J/g) during temperature rise in a hydrated state and crystalline melting enthalpy ($\Delta H_B$: J/g) during temperature rise after drying and melting followed by rapid cooling have to satisfy the following formulae (5) and (6).

$$\Delta H_A / \Delta H_B \geq 0.5 \quad (5)$$

$$\Delta H_B \geq 70 \quad (6)$$

It is possible to obtain the crystalline melting enthalpy ($\Delta H_A$: J/g) by measuring modified EVOH in a hydrated state taken from the barrier layer of the container after hot-water sterilization using a differential scanning calorimeter (DSC) for a peak area in a temperature range from the start to the end of melting during the first temperature rise. Specifically, as described in Examples below, DSC measurement with a hot-water treatment history remained in the modified EVOH is regarded as crystalline melting enthalpy measurement of the modified EVOH after hot-water sterilization.

It is possible to obtain the crystalline melting enthalpy ($\Delta H_B$: J/g) by drying and melting and then rapidly cooling modified EVOH taken from the barrier layer of the container after hot-water sterilization using a differential scanning calorimeter (DSC) to obtain a peak area in a temperature range from the start to the end of melting during temperature rise after that. Specifically, as described in Examples below, DSC measurement without a hot-water treatment history in the modified EVOH allows measurement of a value equivalent to the crystalline melting enthalpy of the modified EVOH before hot-water sterilization. This is because, in DSC measurement, hot-water sterilized modified EVOH is subjected to melting by heating to cancel the influence of a change in the crystal structure caused by the hot-water sterilization.

The present inventors surprisingly found that modified EVOH having a 1,3-diol structure after hot-water sterilization sometimes has more improved barrier properties than that before the sterilization. The present inventors further investigated considering that the effects are partly caused by the crystal structure of the modified EVOH and found that barrier properties are markedly improved when modified EVOH after hot-water sterilization satisfies the above formulae (5) and (6), and thus completed the present invention.

When the container is a multilayer structure described later, the barrier layer containing the modified EVOH may be peeled off from the other layers to be used for measurement of $\Delta H_A$ and $\Delta H_B$.

A preferred melt flow rate (MFR) (at 190° C. under a load of 2160 g) of the modified EVOH is from 0.1 to 30 g/10 min., more preferably from 0.3 to 25 g/10 min., and even more preferably from 0.5 to 20 g/10 min. It is noted that when the melting point is about or over 190° C., the measurements are carried out under a load of 2160 g at a plurality of temperatures not lower than the melting point. The results are plotted, in a semilog graph, with reciprocals of absolute temperatures as abscissa against logarithms of MFRs as ordinate and the preferable MFR is represented by an extrapolation to 190° C.

The modified EVOH may be a mixture of the modified EVOH with unmodified EVOH. Use of such a mixture allows cost reduction. A mass ratio (modified EVOH/unmodified EVOH) of the modified EVOH to the unmodified EVOH in the mixture is preferably from 1/9 to 9/1. From the perspective of more markedly exhibiting the effects of the present invention, the EVOH preferably does not contain unmodified EVOH.

In a case that the modified EVOH is a mixture of two or more different kinds of modified EVOH above or a mixture of the EVOH with unmodified EVOH, average values calculated from a blend weight ratio are used for the contents of the monomer units represented by a, b, and c, the degree of saponification, the MFR, $\Delta H_A$, and $\Delta H_B$.

It is preferred that an oxygen transmission rate of the hot-water sterilized modified EVOH at 20° C. and 85% RH is 100 cc·20 μm/m²·day·atm or less. The oxygen transmission rate is more preferably 10 cc·20 μm/m²·day·atm or less, even more preferably 5 cc·20 μm/m²·day·atm or less, particularly preferably 3 cc·20 μm/m²·day·atm or less, and most preferably 2 cc·20 μm/m²·day·atm or less.

From the perspective of barrier properties, the barrier layer has to contain 96 mass % or more of the modified EVOH based on the resin total in the barrier layer. The content of the modified EVOH is preferably 98 mass % or more and more preferably 99 mass % or more. Even more preferably, the resin in the barrier layer is substantially the modified EVOH only. The contents of resins other than the modified EVOH are small, and the influence of such resins in the DSC measurement of the modified EVOH is extremely small and ignorable. Accordingly, even when the barrier layer contains a resin other than the modified EVOH, it is possible to obtain $\Delta H_A$ and $\Delta H_B$ by the method described in Examples below.

The resin other than the modified EVOH contained in the barrier layer is not particularly limited, and examples of the resin may include thermoplastic resins, such as polyolefin, polyamide, polyester, polystyrene, polyvinyl chloride, acrylic resins, polyurethane, polycarbonate, and polyvinyl acetate.

As long as not inhibiting the effects of the present invention, a resin composition containing additives other than resins may be used as a material for the barrier layer. Examples of the additives may include metal salts, heat stabilizers, antioxidants, ultraviolet absorbers, plasticizers, antistatic agents, lubricants, colorants, fillers, stabilizers, surfactants, desiccants, crosslinkers, fiber reinforcements, and the like. The contents of such other additives in the resin composition is preferably 30 mass % or less, more preferably 20 mass % or less, even more preferably 10 mass % or less, and particularly preferably 5 mass % or less.

Among all, it is preferred to contain alkali metal salt as the metal salt. By making a resin composition containing alkali metal salt in such a manner, interlayer adhesion when laminated to a resin other than the modified EVOH becomes even better. Although cationic species of the alkali metal salt is not particularly limited, it is preferably sodium salt or and potassium salt. Anionic species of the alkali metal salt is also not particularly limited. It is possible to add as salt of carboxylic acid, salt of carbonic acid, salt of hydrogencarbonic acid, salt of phosphoric acid, salt of hydrogenphosphoric acid, salt of boric acid, hydroxide, and the like. It is preferred that an alkali metal salt content in the resin composition is from 10 to 500 ppm in terms of alkali metal elements. The interlayer adhesion is sometimes not obtained sufficiently in a case that the alkali metal salt content is less than 10 ppm, and it is more preferably 50 ppm or more. In contrast, the melt stability is sometimes insufficient in a case that the alkali metal salt content is more than 500 ppm, and it is more preferably 300 ppm or less.

It is also preferred to contain a boron compound as the heat stabilizer. By making a resin composition containing a boron compound in such a manner, it is possible to suppress torque variation during melting by heating. The boron compound used in the present invention is not particularly limited and may include boric acids, borate esters, salts of boric acids, boron hydrides, and the like. Specifically, the boric acids may include orthoboric acid, metaboric acid, tetraboric acid, and the like; the borate esters may include triethyl borate, trimethyl borate, and the like; the salts of boric acids may include alkali metal salts and alkaline earth metal salts of various boric acids mentioned above, borax, and the like. Among these compounds, orthoboric acid (hereinafter, may be described simply as boric acid) is preferred. It is preferred that the boron compound content in the resin composition is preferably from 20 to not more than 2000 ppm in terms of boron elements. The suppression of torque variation during melting by heating sometimes becomes insufficient in a case that the boron compound content is less than 20 ppm, and it is more preferably 50 ppm or more. In contrast, in a case that the boron compound content is more than 2000 ppm, gelation easily occurs and the formability sometimes deteriorates, and it is more preferably 1000 ppm or less.

Moreover, it is also preferred to contain a phosphoric acid compound as the heat stabilizer. By making a resin composition containing a phosphoric acid compound in such a manner, it is possible to prevent coloration during melt molding. The phosphoric acid compound used in the present invention is not particularly limited, and it is possible to use various acids, such as phosphoric acid and phosphorous acid, and salts thereof. Although the salt of phosphoric acid may be contained in any form of primary phosphate, secondary phosphate, and tertiary phosphate, primary phosphate is preferred. Although its cationic species is also not particularly limited, alkali metal salt is preferred. Among them, sodium dihydrogen phosphate and potassium dihydrogen phosphate are preferred. It is preferred that the phosphoric acid compound content in the resin composition is preferably from 5 to 200 ppm in terms of phosphate radicals. The coloration resistance during melt molding sometimes becomes insufficient in a case that the phosphoric acid compound content is less than 5 ppm. In contrast, the melt stability is sometimes insufficient in a case that the phosphoric acid compound content is more than 200 ppm, and it is more preferably 160 ppm or less.

Specific examples of other components may include the following.

Antioxidant: 2,5-di-t-butyl-hydroquinone, 2,6-di-t-butyl-p-cresol, 4,4'-thiobis-(6-t-butylphenol), 2,2'-methylene-bis-(4-methyl-6-t-butylphenol), octadecyl-3-(3',5'-di-t-butyl-4'-hydroxyphenyl)propionate, 4,4'-thiobis-(6-t-butylphenol), and the like.

Ultraviolet absorber: ethylene-2-cyano-3',3'-diphenylacrylate, 2-(2'-hydroxy-5'-methylphenyl)benzotriazole, 2-(2'-hydroxy-3'-t-butyl-5'-methylphenyl) 5-chlorobenzotriazole, 2-hydroxy-4-methoxybenzophenone, 2,2'-dihydroxy-4-methoxybenzophenone, and the like.

Plasticizer: dimethyl phthalate, diethyl phthalate, dioctyl phthalate, wax, liquid paraffin, phosphates, and the like.

Antistatic agent: pentaerythritol monostearate, sorbitan monopalmitate, sulfated polyolefins, polyethylene oxide, Carbowax, and the like.

Lubricant: ethylene bisstearoamide, butyl stearate, and the like.

Colorant: carbon black, phthalocyanine, quinacridon, indoline, azo pigments, red oxide, and the like.

Filler: glass fiber, vallastonite, calcium silicate, and the like.

From the perspective of barrier properties, the content of the modified EVOH in the resin composition is preferably 70 mass % or more, and the modified EVOH is more preferably contained 80 mass % or more, even more preferably 90 mass % or more, and particularly preferably 95 mass % or more.

A method of containing such other components in the modified EVOH is not particularly limited and a known method is employed.

[Container]

Although the container used in the present invention may be made of a single layer structure having the barrier layer only, it is preferably made of a multilayer structure having the barrier layer and other layers from the perspective of functional improvement. The material constituting such other layers may include thermoplastic resins other than the modified EVOH. A container made of a multilayer structure having a modified EVOH layer and layers of another thermoplastic resin other than the modified EVOH layer is more suitable for hot-water sterilization.

Examples of the resin used to form the layers of another thermoplastic resin may include:

high density, medium density, and low density polyethylene;
polyethylene produced by copolymerizing vinyl acetate, acrylic ester, or α-olefin, such as butene and hexene;
ionomer resins;
polypropylene homopolymers;
polypropylene produced by copolymerizing α-olefin, such as ethylene, butene, and hexene;
modified polypropylene with a rubber-based polymer blended therein;
polyolefin, such as resins with maleic anhydride added or grafted to these resins; polyamide; polyester; polystyrene; polyvinyl chloride; acrylic resins; polyurethane; polycarbonate; polyvinyl acetate; and the like. Among them, polyolefin, polyamide, and polyester are preferred.

Each layer of the multilayer structure may be laminated via an adhesive resin layer. The adhesive resin used for the adhesive resin layer may include acid-modified polyolefin and the like. Examples of the acid-modified polyolefin may include olefin-based polymers having unsaturated carboxylic acid or a derivative thereof introduced by chemical bonding and the like.

Layer configuration of the multilayer structure is not particularly limited, and from the perspective of formability, costs, and the like, representative examples may include another thermoplastic resin layer/modified EVOH layer/another thermoplastic resin layer, modified EVOH layer/adhesive resin layer/another thermoplastic resin layer, another thermoplastic resin layer/adhesive resin layer/modified EVOH layer/another thermoplastic resin layer, another thermoplastic resin layer/adhesive resin layer/modified EVOH layer/adhesive resin layer/another thermoplastic resin layer, and the like. Preferred layer configurations of the multilayer structure are another thermoplastic resin layer/modified EVOH layer/another thermoplastic resin layer, another thermoplastic resin layer/adhesive resin layer/modified EVOH layer/another thermoplastic resin layer, and another thermoplastic resin layer/adhesive resin layer/modified EVOH layer/adhesive resin layer/another thermoplastic resin layer. To provide layers of another thermoplastic resin as both outer layers of the modified EVOH layer, the layers of another thermoplastic resin as both outer layers may be layers of different resins or may be layers of the same resin. Among all, the container is preferably made of a multilayer structure having layers containing any one of polyolefin, polyamide, or polyester arranged on both sides of the barrier layer.

Examples of the method of producing the multilayer structure used as the container may include, but not particularly limited to, coextrusion lamination, coextrusion molding, extrusion lamination, dry lamination, extrusion blow molding, coextrusion blow molding, coinjection molding, solution coating, and the like. Among them, coextrusion lamination and coextrusion molding are preferred, and coextrusion molding is more preferred. Lamination of the modified EVOH layer to the layer of another thermoplastic resin by the above methods allows easy and reliable production of the multilayer structure. The multilayer structure is obtained as a sheet or a film by the above methods, and examples of the method of molding the sheet or the film thus obtained may include vacuum molding, pressure molding, vacuum-pressure molding, blow molding, and the like. Such molding is usually carried out in a temperature range of not more than the melting point of EVOH.

[Hot-Water Sterilized Package]

The package of the present invention is a hot-water sterilized package, comprising the container filled with contents. Examples of the contents to fill the container may include, but not particularly limited to, foods, beverages, medical products, and the like.

The hot-water sterilization herein means sterilization from 60° C. to 140° C. in the presence of moisture, and specific examples may include retorting and boiling. Examples of the method of exposing the package to moisture may include a method comprising contacting with vapor, a method comprising immersing in hot water, a method comprising showering the package with hot water, and the like. The hot-water sterilized package herein means a package to which the above sterilization is applied.

Retorting is a method of sterilizing microorganisms, such as mold, yeast, and bacteria, by heat under pressure to store foods and the like. In general, a package having a container filled with foods and the like, where the container has an intermediate layer of a gas barrier resin, is sterilized under pressure under conditions from 105° C. to 140° C., from 0.15 to 0.3 MPa, and from 5 to 120 min. There are retort systems of a steam type using heated steam, a hot-water immersion type using pressurized superheated water, and the like to be appropriately used in accordance with sterilization conditions of the contents, such as foods.

Boiling is a sterilization method with hot water to store foods and the like. In general, while the conditions may differ depending on the contents, a package having a container filled with foods and the like, where the container has an intermediate layer of a gas barrier resin, is sterilized under conditions from 60° C. to 100° C., at an atmospheric pressure, and from 10 to 120 min. Boiling is usually carried out using a hot water chamber, which includes a batch type for immersion in the hot water chamber at a constant temperature to be taken out after a certain time and a continuous type for sterilization by putting through the hot water chamber like a tunnel.

It is possible to produce the package of the present invention by filling the container with the contents, followed by the hot-water sterilization.

Since the hot-water sterilized package of the present invention is excellent in gas barrier properties, quality degradation of contents, such as foods and medical products, is inhibited for a long period.

EXAMPLES

Although further detailed descriptions are given below to the present invention by Examples, the present invention is not limited to Examples.

Production Example 1

(1) Synthesis of Modified EVAc

To a 250 L pressure reaction vessel provided with a jacket, a stirrer, a nitrogen inlet, an ethylene inlet, and an initiator addition port, 120 kg of vinyl acetate ($R^5$ is a methyl group in the formula (II): hereinafter, referred to as VAc), 18 kg of methanol (hereinafter, may be referred to as MeOH), and 0.9 kg of 2-methylene-1,3-propanediol diacetate ($R^1$, $R^2$, $R^3$, and $R^4$ are hydrogen atoms and $R^6$ and $R^7$ are methyl groups in the formula (III): hereinafter, referred to as MPDAc) were charged, and the temperature was raised to 60° C., and after that, nitrogen bubbling was carried out for 30 minutes to purge inside the reaction vessel with nitrogen. Subsequently, ethylene was introduced to have a reaction vessel pressure (ethylene pressure) of 3.4 MPa. After the temperature in the reaction vessel is adjusted at 60° C., 36 g of 2,2'-azobis(2,4-dimethylvaleronitrile) ("V-65" produced by Wako Pure Chemical Industries, Ltd.) as an initiator was added in the form of methanol solution to initiate polymerization. During the polymerization, the ethylene pressure was maintained at 3.4 MPa and the polymerization temperature at 60° C. After 6 hours, when the conversion of VAc became 45%, the polymerization was stopped by cooling. After removing ethylene by opening the reaction vessel, a nitrogen gas was bubbled to completely remove ethylene. Subsequently, after unreacted VAc was removed under reduced pressure, MeOH was added to the modified ethylene-vinyl acetate copolymer (hereinafter, may be referred to as modified EVAc) to which a structural unit derived from MPDAc was introduced by copolymerization to have a 20 mass % MeOH solution.

(2) Saponification of Modified EVAc

To a 500 L reaction vessel provided with a jacket, a stirrer, a nitrogen inlet, a reflux condenser, and a solution addition port, a 20 mass % MeOH solution of the modified EVAc obtained in (1) was charged. The temperature was raised to 60° C. while blowing nitrogen into the solution, and 0.5 equivalents of sodium hydroxide with respect to vinyl acetate units in the modified EVAc were added in the form of MeOH solution of 2 N. After completion of adding the MeOH sodium hydroxide solution, saponification reaction proceeded by stirring for 2 hours while keeping the temperature in the system at 60° C. After that, acetic acid was added to stop the saponification reaction. After that, while heating and stirring from 60° C. to 80° C., ion exchange water was added to drain MeOH outside the reaction vessel and to precipitate modified EVOH. The precipitated modified EVOH was collected and ground with a mixer. The modified EVOH powder thus obtained was added in a 1 g/L aqueous acetic acid solution (bath ratio of 20:proportion of 1 kg of the powder to 20 L of the aqueous solution) and it was stirred and washed for 2 hours. It was deliquored and was further put into a 1 g/L aqueous acetic acid solution (bath ratio of 20) and it was stirred and washed for two hours. An operation of putting one obtained by deliquoring it into ion exchange water (bath ratio of 20) for stirring and washing for 2 hours and deliquoring it was repeated three times to carry out purification. Subsequently, it was stirred and immersed in 10 L of an aqueous solution containing 0.5 g/L of acetic acid and 0.1 g/L of sodium acetate for 4 hours and then deliquored, and it was dried at 60° C. for 16 hours to obtain roughly dried modified EVOH. The modified EVOH thus obtained had a melt flow rate (MFR) (at 190° C. under a load of 2160 g) of 1.5 g/10 min.

(3) Production of Modified EVOH Hydrous Pellet

To a 80 L stirring vessel provided with a jacket, a stirrer, and a reflux condenser, the roughly dried modified EVOH obtained in (2), water, and MeOH were charged and the temperature was raised to 80° C. for dissolution. The solution was extruded in a liquid mixture of water/MeOH=90/10 cooled at 5° C. through a tube having a diameter of 4 mm to be precipitated in the form of strand, and the strand was cut with a strand cutter into pellets to obtain modified EVOH hydrous pellets. The moisture content of the modified EVOH hydrous pellets thus obtained was measured by a halogen moisture meter "HR 73" manufactured by Mettler and it was 60 mass %.

(4) Production of Modified EVOH Composition Pellet

In a 1 g/L aqueous acetic acid solution (bath ratio of 20), the modified EVOH hydrous pellets obtained in (3) above was added and it was stirred and washed for 2 hours. It was deliquored and was further added in a 1 g/L aqueous acetic acid solution (bath ratio of 20) and it was stirred and washed for 2 hours. After deliquoring, the aqueous acetic acid solution was renewed and same operation was carried out. An operation of putting one, obtained by washing with the aqueous acetic acid solution and then deliquoring it, into ion exchange water (bath ratio of 20) for stirring and washing for 2 hours and deliquoring it was repeated 3 times to carry out purification, and thus modified EVOH hydrous pellets from which the catalyst residue during the saponification reaction was removed were obtained. The hydrous pellets were added in an aqueous solution (bath ratio of 20) having a sodium acetate concentration of 0.5 g/L, an acetic acid concentration of 0.8 g/L, and a phosphoric acid concentration of 0.005 g/L for immersion for 4 hours while periodically stirred. They were deliquored and dried at 80° C. for 3 hours and at 105° C. for 16 hours, thereby obtaining modified EVOH composition pellets.

(5) Content of Each Structural Unit in Modified EVAc

In the modified EVAc, the content of ethylene units (a mol % in the formula (IV)), the content of structural units derived from vinyl acetate (b mol % in the formula (IV)), and the content of structural units derived from MPDAc (c mol % in the formula (IV)) were calculated by $^1$H-NMR measurement of the modified EVAc before saponification.

Firstly, a small amount of the MeOH solution of modified EVAc obtained in (1) was sampled and modified EVAc was precipitated in ion exchange water. The precipitate was collected and dried at 60° C. under vacuum, and thus dried modified EVAc was obtained. Next, the dried modified EVAc thus obtained was dissolved in dimethyl sulfoxide (DMSO)-d6 containing tetramethylsilane as the internal standard material and measured at 80° C. using 500 MHz $^1$H-NMR ("GX-500" manufactured by JEOL Ltd.).

Figure 1:
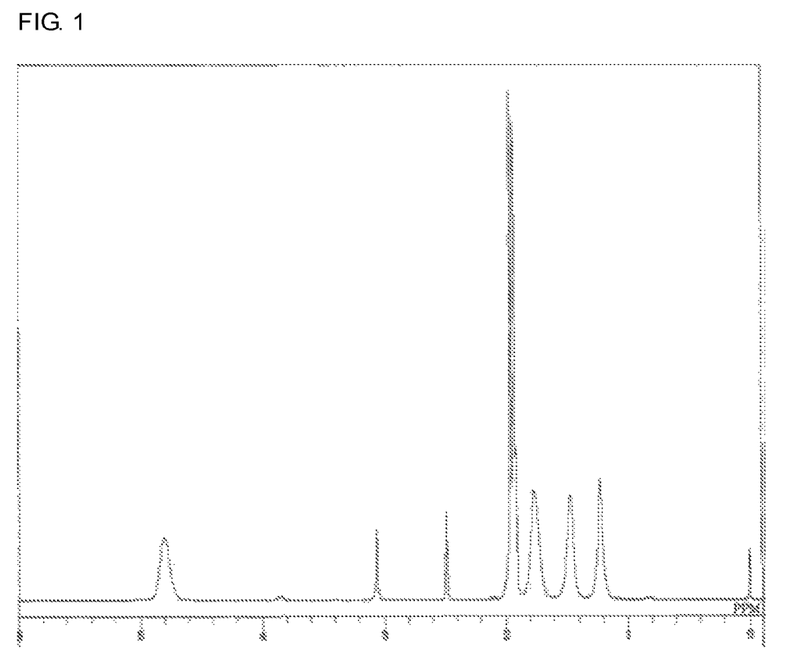
FIG. 1 is a $^1$H-NMR spectrum of a modified EVAc obtained in Example 1

FIG. 1 illustrates, as a $^1$H-NMR spectrum of modified EVAc, a spectrum of the modified EVAc obtained in Example 1. Each peak in the spectrum is assigned as follows:

from 0.6 to 1.0 ppm: methylene proton (4H) in a terminal region of ethylene unit;

from 1.0 to 1.85 ppm: methylene proton (4H) in an intermediate region of ethylene unit, methylene proton (2H) in main chain of structural unit derived from MPDAc, methylene proton (2H) of vinyl acetate unit;

from 1.85 to 2.1 ppm: methyl proton (6H) of structural unit derived from MPDAc and methyl proton (3H) of vinyl acetate unit;

from 3.7 to 4.1 ppm: methylene proton (4H) in side chain of structural unit derived from MPDAc;

from 4.4 to 5.3 ppm: methine proton (1H) of vinyl acetate unit.

In accordance with the above assignment, where the integral value from 0.6 to 1.0 ppm is x, the integral value from 1.0 to 1.85 ppm is y, the integral value from 3.7 to 4.1 ppm is z, and the integral value from 4.4 to 5.3 ppm is w, the ethylene unit content (a: mol %), the vinyl ester unit content (b: mol %), and the content of structural units derived from MPDAc (c: mol %) are calculated according to the following formulae, respectively.

$$a=(2x+2y-z-4w)/(2x+2y+z+4w)\times 100$$

$$b=8w/(2x+2y+z+4w)\times 100$$

$$c=2z/(2x+2y+z+4w)\times 100$$

As a result of calculating in the above method, the ethylene unit content (a) was 27.0 mol %, the vinyl ester unit content (b) was 72.5 mol %, the content (c) of structural units derived from MPDAc was 0.5 mol %. The values of a, b, and c in the modified EVAc were same as the values of a, b, and c in the modified EVOH after saponification.

(6) Degree of Saponification of Modified EVOH

Figure 2:
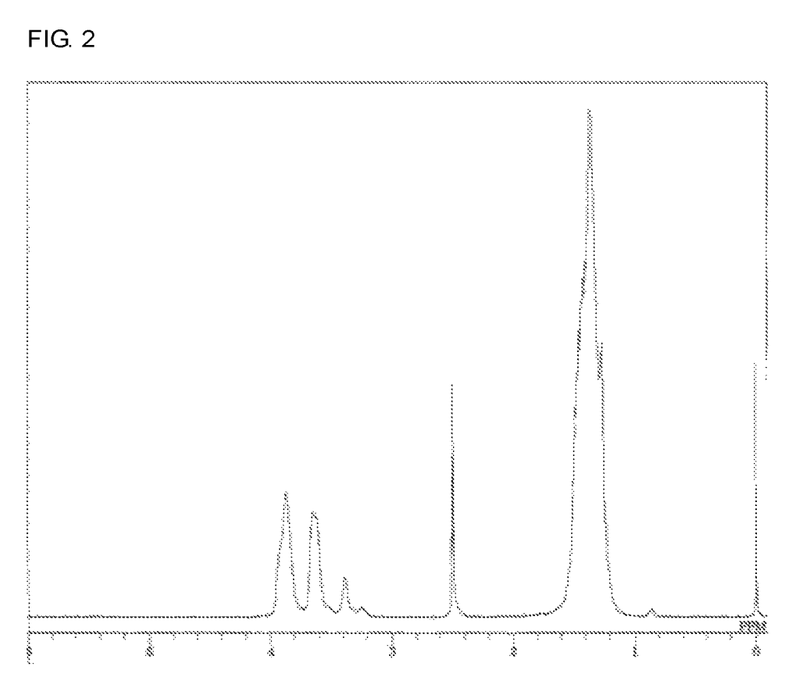
FIG. 2 is a $^1$H-NMR spectrum of a modified EVOH obtained in Example 1

The modified EVOH after saponification was also subjected to $^1$H-NMR measurement similarly. The roughly dried modified EVOH obtained in (2) above was dissolved in dimethyl sulfoxide (DMSO)-d6 containing tetramethylsilane as the internal standard material and tetrafluoroacetic acid (TFA) as an additive and measured at 80° C. using 500 MHz $^1$H-NMR ("GX-500" manufactured by JEOL Ltd.). FIG. 2 illustrates, as an example of a $^1$H-NMR spectrum of modified EVOH, a spectrum of the modified EVOH obtained in Example 1. Since the peak intensity from 1.85 to 2.1 ppm decreased drastically, it is clear that the ester group contained in the structural units derived from MPDAc, in addition to the ester group contained in vinyl acetate, was also saponified to be hydroxyl group. From the $^1$H-NMR spectrum obtained in Example 1 as well, such a decrease of the peak intensity from 1.85 to 2.1 ppm was observed. The degree of saponification was calculated from the peak intensity ratio of the methyl proton of vinyl acetate unit (from 1.85 to 2.1 ppm) and the methine proton of vinyl alcohol unit (from 3.15 to 4.15 ppm). The degree of saponification of the modified EVOH in Example 1 was 99.9 mol % or more.

(7) Melting Point of Modified EVOH

Measurement of the modified EVOH composition pellets obtained in (4) above was performed according to JIS K7121 by raising the temperature from 30° C. to 215° C. at a rate of 10° C./min., and after that, rapidly cooling it to −35° C. at 100° C./min., and again from −35° C. to 195° C. at a rate of temperature rise of 10° C./min. (differential scanning calorimeter (DSC) "RDC220/SSC5200H" manufactured by Seiko Instruments & Electronics Ltd.). For temperature calibration, indium and lead were used. The peak melting temperature (Tpm) was obtained from the 2nd-run chart in accordance with the JIS above to define it as the melting point of modified EVOH. The melting point was 187° C.

(8) Sodium Salt Content and Phosphoric Acid Compound Content in Modified EVOH Composition In a teflon (registered trademark) pressure vessel, 0.5 g of the modified EVOH composition pellets obtained in (4) above was placed and 5 mL of concentrated nitric acid was added there for decomposition at room temperature for 30 minutes. After 30 minutes, the lid was closed for decomposition by heating at 150° C. for 10 minutes and subsequently at 180° C. for 5 minutes with a wet digestion apparatus ("MWS-2" manufactured by Actac Corp.), and after that, it was cooled to room temperature. The process liquid was poured into a 50 mL measuring flask (made of TPX) and diluted with pure water. With this solution, analysis of contained metal was carried out by an ICP emission spectrophotometer ("OPTIMA4300DV" manufactured by Perkin-Elmer Inc.) and the contents of sodium elements and phosphorus elements were obtained. The sodium salt content was 150 ppm in terms of sodium elements, and the phosphoric acid compound content was 10 ppm in terms of phosphate radicals.

Production Examples 2 Through 14

Modified EVAc, modified EVOH, and modified EVOH composition pellets were prepared and analyzed in the same manner as that in Production Example 1 except for changing the polymerization conditions in Production Example 1 (1) as shown in Table 1. The results are shown in Table 1.

TABLE 1

| | Polymerization Condition | | | | | | | | Modified EVOH | | |
|---|---|---|---|---|---|---|---|---|---|---|---|
| | Initial Charge | | | | | Polymerization Temperature | Polymerization Time | Final Conversion | a Content | c Content | Degree of Saponification (DS) |
| | Vinyl Acetate | Methanol | Modifier | | Ethylene Pressure | Initiator | | | | | |
| | kg | kg | Type [1)] | kg | MPa | g | ° C. | hours | % | mol % | mol % | mol % |
| Production Example 1 | 120 | 18 | 1 | 0.9 | 3.4 | 36 | 60 | 6 | 45 | 27 | 0.5 | ≥99.9 |
| Production Example 2 | 120 | 12 | 1 | 1.9 | 3.5 | 48 | 60 | 6 | 48 | 27 | 1.0 | ≥99.9 |
| Production Example 3 | 120 | 12 | 1 | 2.7 | 3.5 | 48 | 60 | 6.5 | 48 | 27 | 1.5 | ≥99.9 |
| Production Example 4 | 110 | 11 | 1 | 0.8 | 4.1 | 44 | 60 | 4.5 | 40 | 32 | 0.5 | ≥99.9 |
| Production Example 5 | 110 | 8 | 1 | 1.7 | 4.2 | 44 | 60 | 4.5 | 40 | 32 | 1 | ≥99.9 |
| Production Example 6 | 100 | 10 | 1 | 1 | 4.9 | 44 | 60 | 6 | 45 | 38 | 0.5 | ≥99.9 |
| Production Example 7 | 90 | 9 | 1 | 0.4 | 5.7 | 72 | 60 | 6 | 40 | 44 | 0.2 | ≥99.9 |
| Production Example 8 | 100 | 30 | None | — | 2.9 | 15 | 60 | 6 | 46 | 27 | — | ≥99.9 |
| Production Example 9 | 100 | 30 | None | — | 3.7 | 20 | 60 | 4 | 44 | 32 | — | ≥99.9 |
| Production Example 10 | 90 | 27 | None | — | 4.5 | 18 | 60 | 6 | 48 | 38 | — | ≥99.9 |
| Production Example 11 | 110 | 6 | 1 | 2.4 | 4.3 | 44 | 60 | 6 | 40 | 32 | 1.4 | ≥99.9 |
| Production Example 12 | 110 | 2 | 1 | 6.2 | 4.3 | 88 | 60 | 7 | 35 | 32 | 3.9 | ≥99.9 |

TABLE 1-continued

| | Polymerization Condition | | | | | | | | | Modified EVOH | | |
| --- | --- | --- | --- | --- | --- | --- | --- | --- | --- | --- | --- | --- |
| | Initial Charge | | | | | Polymer- | Polymer- | | | | | Degree of Saponi- |
| | Vinyl Acetate | Methanol | Modifier | | Ethylene Pressure | Initiator | ization Temperature | ization Time | Final Conversion | a Content | c Content | fication (DS) |
| | kg | kg | Type [1] | kg | MPa | g | ° C. | hours | % | mol % | mol % | mol % |
| Production Example 13 | 120 | 12 | 1 | 4.9 | 3.5 | 48 | 60 | 6 | 32 | 27 | 3.0 | ≥99.9 |
| Production Example 14 | 90 | 9 | 1 | 1.9 | 5.8 | 72 | 60 | 6 | 60 | 44 | 1.4 | ≥99.9 |

[1] Modifier 1: 2-methylene-1,3-propanediol diacetate

Example 1

(1) Preparation of Multilayer Sheet

The modified EVOH composition pellets obtained in Production Example 1 was used as a material and formed into a film to have 3-layer configuration of polypropylene layer/modified EVOH composition layer/polypropylene layer using a 2-type 3-layer coextruder to prepare a multilayer sheet. At this point, each polypropylene layer had a thickness of 360 μm and the modified EVOH layer had a thickness of 80 μm. The multilayer sheet thus obtained was cut into A4 size, heat sealed on three sides, fed with 500 mL of distilled water inside, and heat sealed on the remained side to obtain a package before hot-water sterilization. The package before hot-water sterilization was immersed in hot water at 120° C. for 30 minutes for hot-water sterilization (hot water immersion) to obtain a hot-water sterilized package.

(2) Measurement of $\Delta H_A$ and $\Delta H_B$

Using a differential scanning calorimeter (DSC) "Q2000" manufactured by TA Instruments Inc., $\Delta H_A$ and $\Delta H_B$ were obtained by DSC measurement in accordance with JIS K7121. For temperature calibration, indium was used. The preparation method and the measurement procedure of a sample used in each measurement were as follows. The results are shown in Table 1.

(2-1) Measurement of $\Delta H_A$

From the package after hot-water sterilization, an approximately 2 mg section in terms of modified EVOH was cut. Further, from the section, the polypropylene layers as the inner and outer layers were delaminated to obtain a section of the modified EVOH layer. The total amount of the section thus obtained was sealed in a hermetic pan (manufactured by TA Instruments Inc.) and subjected to DSC measurement by raising the temperature from 30° C. to 241° C. at a rate of 10° C./min. The crystalline melting enthalpy ($\Delta H_A$: J/g) was obtained by a peak area in a temperature range from the start to the end of melting during the first temperature rise in the DSC curve thus obtained. In the present measurement, the hermetic pan was used to prevent evaporation of water vapor during the measurement.

(2-2) Measurement of $\Delta H_B$

From the package after hot-water sterilization, an approximately 2 mg section in terms of modified EVOH was cut. Further, from the section, the polypropylene layers as the inner and outer layers were delaminated to obtain a section of the modified EVOH layer. The total amount of the section thus obtained was sealed in an aluminum pan (manufactured by TA Instruments Inc.) and subjected to DSC measurement by raising the temperature from 30° C. to 241° C. at a rate of 10° C./min., followed by rapid cooling to 92° C. at 10° C./min., and again temperature rise from 92° C. to 241° C. at a rate of 10° C./min. The crystalline melting enthalpy ($\Delta H_B$: J/g) was obtained by a peak area in a temperature range from the start to the end of melting during the second temperature rise in the DSC curve thus obtained.

(3) Measurement of Oxygen Transmission Rate of Package before Hot-Water Sterilization A sheet prepared by cut opening the package before hot-water sterilization thus obtained was moisture conditioned for 2 months in the conditions of 20° C. and inner layer 100% RH/outer layer 65% RH to be served for measurement of the oxygen transmission rate in the same conditions ("OX-TORAN MODEL 2/21" manufactured by MOCON, Inc.). The results are shown in Table 2.

TABLE 2

| | Modified EVOH | | | | | | | Oxygen Transmission Rate [2] | | Difference |
| --- | --- | --- | --- | --- | --- | --- | --- | --- | --- | --- |
| | Production Example | a Content mol % | Modifier [1] | c Content mol % | Degree of Saponification (DS) mol % | $\Delta H_A/\Delta H_B$ | $\Delta H_B$ (J/g) | Before Hot-Water Sterilization | After Hot-Water Sterilization | in Oxygen Transmission Rate [2] |
| Example 1 | 1 | 27 | 1 | 0.5 | ≥99.9 | 0.55 | 78 | 1.4 | 0.6 | 0.8 |
| Example 2 | 2 | 27 | 1 | 1.0 | ≥99.9 | 0.53 | 74 | 2.2 | 1 | 1.2 |
| Example 3 | 3 | 27 | 1 | 1.5 | ≥99.9 | 0.52 | 70 | 2.6 | 1.3 | 1.3 |
| Example 4 | 4 | 32 | 1 | 0.5 | ≥99.9 | 0.57 | 76 | 1.8 | 0.9 | 0.9 |
| Example 5 | 5 | 32 | 1 | 1.0 | ≥99.9 | 0.55 | 73 | 2.4 | 1.6 | 0.8 |
| Example 6 | 6 | 38 | 1 | 0.5 | ≥99.9 | 0.66 | 74 | 3.4 | 2.2 | 1.2 |
| Example 7 | 7 | 44 | 1 | 0.2 | ≥99.9 | 0.63 | 75 | 5.3 | 4 | 1.3 |
| Comparative Example 1 | 8 | 27 | unmodified | — | ≥99.9 | 0.56 | 84 | 1.3 | 1.6 | −0.3 |

TABLE 2-continued

| | | Modified EVOH | | | | | Oxygen Transmission Rate [2] | | Difference |
| | Production Example | a Content mol % | Modifier [1] | c Content mol % | Degree of Saponification (DS) mol % | $\Delta H_A/\Delta H_B$ | $\Delta H_B$ (J/g) | Before Hot-Water Sterilization | After Hot-Water Sterilization | in Oxygen Transmission Rate [2] |
|---|---|---|---|---|---|---|---|---|---|---|
| Comparative Example 2 | 9 | 32 | unmodified | — | ≥99.9 | 0.58 | 82 | 2 | 2.3 | −0.3 |
| Comparative Example 3 | 10 | 38 | unmodified | — | ≥99.9 | 0.59 | 77 | 3.3 | 3.7 | −0.4 |
| Comparative Example 4 | 11 | 32 | 1 | 1.4 | ≥99.9 | 0.48 | 70 | 2.7 | 3 | −0.3 |
| Comparative Example 5 | 12 | 32 | 1 | 3.9 | ≥99.9 | 0.4 | 36 | 4 | 4.3 | −0.3 |
| Comparative Example 6 | 13 | 27 | 1 | 3.0 | ≥99.9 | 0.4 | 49 | 3.5 | 4.4 | −0.9 |
| Comparative Example 7 | 14 | 44 | 1 | 1.0 | ≥99.9 | 0.57 | 65 | 5 | 5.5 | −0.5 |

[1] modifier 1: 2-methylene-1,3-propanediol diacetate
[2] unit: cc · 20 μm/m² · day · atm (4) Measurement of Oxygen Transmission Rate of Package after Hot-Water Sterilization A sheet prepared by cut opening the package after hot-water sterilization was moisture conditioned for 2 months in the conditions of 20° C. and inner layer 100% RH/outer layer 65% RH to be served for measurement of the oxygen transmission rate in the same conditions ("OX-TORAN MODEL 2/21" manufactured by MOCON, Inc.). The results are shown in Table 2.

Examples 2 Through 7, Comparative Examples 1 Through 7

A package was prepared and evaluated in the same manner as that in Example 1 except for changing the type of EVOH (EVOH composition) as shown in Table 1. The results are shown in Table 2.

The hot-water sterilized packages of the present invention (Examples 1 through 7) of the modified EVOH with monomer units having a 1,3-diol structure were excellent in oxygen barrier properties after hot-water sterilization. In contrast, the cases of using unmodified EVOH (Comparative Examples 1 through 3) and using modified EVOH not satisfying $\Delta H_A$ and $\Delta H_B$ defined in the present invention (Comparative Examples 4 through 7) had lower oxygen barrier properties after hot-water sterilization.

The invention claimed is:

1. A hot-water sterilized package, comprising a container filled with contents, wherein
the container comprises a barrier layer,
the barrier layer comprises 96 mass % or more of a modified ethylene-vinyl alcohol copolymer based on a total amount of resin,
the modified ethylene-vinyl alcohol copolymer is represented by a formula (I), contents (mol %) of a, b, and c based on the total monomer units satisfy formulae (1) through (3), a degree of saponification (DS) defined by a formula (4) is 99 mol % or more, and in measurement using a differential scanning calorimeter (DSC), crystalline melting enthalpy ($\Delta H_A$: J/g) during temperature rise in a hydrated state, wherein the hydrated state is produced by sterilization at a temperature from 60° C. to 140° C. in the presence of moisture, and crystalline melting enthalpy ($\Delta H_B$: J/g) during temperature rise after drying and melting followed by rapid cooling satisfy formulae (5) and (6), wherein measurement by DSC is performed by raising the temperature from 30° C. to 241° C. at a rate of 10° C./min., followed by rapid cooling to 92° C. at 10° C/min;

wherein in the formula (I), each of $R^1$, $R^2$, $R^3$, and $R^4$ is a hydrogen atom and each of X, Y, and Z independently denotes a hydrogen atom, a formyl group, or an alkanoyl group having a carbon number from 2 to 10

$$22 \leq a \leq 40 \tag{1}$$

$$0.2 \leq c \leq 1.5 \tag{2}$$

$$[100-(a+c)] \times 0.9 \leq b \leq [100-(a+c)] \tag{3}$$

DS=[(Total Number of Moles of Hydrogen Atoms in X, Y, and Z)/(Total Number of Moles of X, Y, and Z)]×100  (4)

$$\Delta H_A/\Delta H_B \geq 0.5 \tag{5}$$

$$\Delta H_B \geq 70 \tag{6); and}$$

wherein the package has a lower oxygen transmission rate after hot-water sterilization compared to the oxygen transmission before hot-water sterilization.

2. The package according to claim 1, wherein each of X, Y, and Z is independently a hydrogen atom or an acetyl group.

3. The package according to claim 1, wherein the container comprises a multilayer structure having layers comprising any of polyolefin, polyamide, or polyester arranged on both sides of the barrier layer.

4. A method of producing the package according to claim 1, comprising: filling the container with the contents; and then subjecting the container to sterilization at a temperature from 60° C. to 140° C. in the presence of moisture.

* * * * *